(12) United States Patent
Jolidon et al.

(10) Patent No.: US 7,790,763 B2
(45) Date of Patent: Sep. 7, 2010

(54) SUBSTITUTED PHENYL METHANONE DERIVATIVES

(75) Inventors: Synese Jolidon, Blauen (CH); Robert Narquizian, St. Louis (FR); Roger David Norcross, Olsberg (CH); Emmanuel Pinard, Linsdorf (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 1227 days.

(21) Appl. No.: 11/332,999

(22) Filed: Jan. 17, 2006

(65) Prior Publication Data

US 2006/0160788 A1    Jul. 20, 2006

(30) Foreign Application Priority Data

Jan. 18, 2005    (EP)    ................... 05100280

(51) Int. Cl.
*A61K 31/40* (2006.01)
*C07D 295/27* (2006.01)

(52) U.S. Cl. ....................... 514/423; 548/531
(58) Field of Classification Search ................. 514/423; 548/531
See application file for complete search history.

(56) References Cited

U.S. PATENT DOCUMENTS

| | | | |
|---|---|---|---|
| 3,933,802 | A | 1/1976 | Ferrini et al. |
| 4,244,871 | A | 1/1981 | Kosary et al. |
| 6,001,854 | A | 12/1999 | Ognyanov et al. |
| 2005/0059668 | A1 | 3/2005 | Alberati-Giani et al. |
| 2005/0070539 | A1 | 3/2005 | Alberati-Giani et al. |
| 2005/0209241 | A1 | 9/2005 | Jolidon et al. |
| 2007/0299071 | A1* | 12/2007 | Jolidon et al. ............ 514/235.5 |

FOREIGN PATENT DOCUMENTS

| | | |
|---|---|---|
| EP | 0 171 636 | 2/1985 |
| EP | 0 624 581 | 11/1994 |
| WO | WO 99/44596 | 9/1999 |
| WO | WO 99/45011 | 9/1999 |
| WO | WO 01/81308 | 11/2001 |
| WO | WO 02/22612 | 3/2002 |
| WO | WO 03/004480 | 1/2003 |
| WO | WO 03/035602 | 5/2003 |
| WO | WO 2004/037800 | 5/2004 |
| WO | WO 2005/058882 | 6/2005 |
| WO | WO 2005/110983 | 11/2005 |

OTHER PUBLICATIONS

Chabrier et al. "Preparation of N-phhenyl . . . " CA 136:69731 (2002.*
Praysse et al. "Aminopyrimidines . . . " CA 147:9933 (2007).*
Tani et al. "Preparation of aryll . . . " CA 138:187795 (2003).*
King "Bioisosteres . . . " Med. Chem. Principle and Practice p. 206-209 (1994).*
Exhibit I.*

Lewis D.A. & Lieberman J.A, Neuron. vol. 28, pp. 325-334 (2000).
Vandenberg R. J. & Aubrey K. R., Exp. Opin. Ther. Targets vol. 5(4) pp. 507-518 (2001).
Nakazato A. & Okuyama S., Exp. Opin. Ther. Patents vol. 10(1) pp. 75-98 (2000).
Sharma T., Br. J. Psychiatry, vol. 174 (Suppl. 38) pp. 44-51 (1999).
Javitt D. C. et al., Biol. Psychiatry, vol. 45 pp. 668-679 (1999).
Mohn A. R., Cell vol. 98 pp. 427-436 (1999).
Bliss, T. V. & Collingridge G. L., Nature, vol. 361 pp. 31-39 (1993).
Tang J. P. et al., Nature, vol. 401, pp. 63-69 (1999).
Gainetdinov R. R. et al., Trends in Pharm. Sci. vol. 23(8) pp. 367-373 (2002).
Lopez-Corcuera B, et al., Mol. Mem. Biol. vol. 18 pp. 13-20 (2001).
Bergeron R. et al., Proc. Natl. Acad. Sci. USA vol. 95, pp. 15730-15734 (1998).
Chen et al., J. Neurophysiol. vol. 89(2) pp. 691-703 (2003).
Armer R. E. & Miller D. J., Exp. Opin. Ther. Patents vol. 11(4) pp. 563-572 (2001).
Pralong E. et al., Prog. in Neurobiol. vol. 67, pp. 173-202 (2002).
Carlsson M. L., J. Neural Trans. vol. 105, pp. 525-535 (1998).
Kwong et al, Org. Lett. 4, pp. 581-584 (2002).
Kuwano et al., JOC 67, pp. 6479-6486 (2002).
Chem. Abstract XP-002299148.
Caulfield W. L. et al., Journal of Med. Chem. vol. 44(17) pp. 2679-2682 (2001).
Chem. Abstract XP-002299149.
Chemical Abstracts Service, Apr. 23, 2003, XP002308402, Database accession No. 2003: 2142911 Chemcats & Catalog: AsInExExpress Gold.
Chemical Abstracts Service, Jun. 6, 2003, XP002308481 & Database Chemcats.
Chemical Abstracts Service, Jan. 1, 2004, XP002308405, Database accession No. 2003:2872406 Chemcats & Catalog: Ambinter Stock Screening Collection.

(Continued)

*Primary Examiner*—Celia Chang
(74) *Attorney, Agent, or Firm*—George W. Johnston; Patricia S. Rocha-Tramaloni; Kimberly J. Prior

(57) ABSTRACT

The present invention relates to compounds of formula I

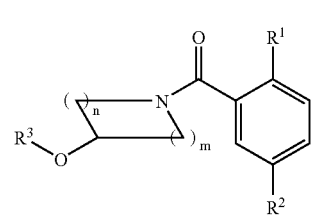

wherein
    $R^1$, $R^2$, $R^3$, n, and m, are as defined in the specification and to pharmaceutically acceptable acid addition salts thereof.

These compounds are good inhibitors of the glycine transporter 1 (GlyT-1) and are useful for the treatment of CNS disorders such as schizophrenia, cognitive impairment, and Alzheimer's disease.

18 Claims, No Drawings

OTHER PUBLICATIONS

Chemical Abstracts Service, Jan. 1, 2004, XP002308403, Database accession No. 2004:591813 & Catalog: Ambinter Stock Screening Collection.
Chemical Abstracts Service, Jan. 1, 2004, XP002308404, Database accession No. 2004:660630 & Catalog: Ambinter Screening Library.
Chemical Abstracts Service, XP002308978.
Chemical Abstracts Service, XP002308979; CHEMCATS No. 2003:1026314.
Chemical Abstracts Service, XP002308980; CHEMCATS No. 2001;2814605.
Chemical Abstracts Service, XP002308981; CHEMCATS No. 2002:2063001.
Chemical Abstracts Service, XP002308983; CHEMCATS No. 2003:1026533.
Chemical Abstracts Service, XP002308984; CHEMCATS No. 2002:2288893.
Chemical Abstracts Service, XP002308985; CHEMCATS No. 2003:709504.
Chemical Abstracts Service, XP002308986; CHEMCATS No. 2003:709503.
Chemical Abstracts Service, XP002308987; CHEMCATS No. 2003:709505.
Chemical Abstracts Service, XP002308988; CHEMCATS No. 2004:1498769.
Chemical Abstracts Service, XP002308989; CHEMCATS No. 2002:2386068.
Chemical Abstracts Service, XP002308990; CHEMCATS No. 2002:2894607.
Chemical Abstracts Service, XP002308991; CHEMCATS No. 2003:3342164.
Chemical Abstracts Service, XP002308992; CHEMCATS No. 2003:3345505.
Chemical Abstracts Service, XP002308993; CHEMCATS No. 2003:3346187.
Chemical Abstracts Service, XP002309007; CHEMCATS No. 2004:660630.
Abstract corresponding to Document B5—WO 03/035602.
Cabiddu et al., Journal of Organometallic Chemistry, 1991, 419(1-2) 1-8.
Collins, et al., J. Med. Chem. 1998, 41, p. 5037-5054.
Yamanaka et al., Tetrahedron Lett., 1996, vol. 37, p. 1829-1832.
Guisado et al., Tetrahedron Lett, 2002, vol. 43, p. 7105-7109.
Caufield, et al., Journal of Medicinal Chem., vol. 44(17) pp. 2679-2682 (2001).
Souers et al., Bioorganic & Medicinal Chem. Letters, vol. 14(19) pp. 4883-4886 (2004).
Wolin et al., Bioorganic & Medicinal Chem. vol. 12, pp. 4511-4532 (2004).
Lowe, John A., III, Expert Opin. On the Patents vol. 15 (11) pp. 1657-1662 (2005).

* cited by examiner

SUBSTITUTED PHENYL METHANONE DERIVATIVES

PRIORITY DATA

This application claims the benefit of European Application No. 05100280.6, filed Jan. 18, 2005, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron,* 28:325-33, 2000). For decades research has focused on the "dopaminergic hyperactivity" hypothesis which has led to therapeutic interventions involving blockade of the dopaminergic system (Vandenberg R J and Aubrey K R., *Exp. Opin. Ther. Targets,* 5(4): 507-518, 2001; Nakazato A and Okuyama S, et al., *Exp. Opin. Ther. Patents,* 10(1): 75-98, 2000). This pharmacological approach poorly address negative and cognitive symptoms which are the redictors of functional outcome (Sharma T., *Br. J. Psychiatry,* 174(suppl. 28): 44-51, 1999).

A complementary model of schizophrenia was proposed in the mid-1960s based upon the psychotomimetic action caused by the blockade of the glutamate system by compounds like phencyclidine (PCP) and related agents (ketamine) which are non-competitive NMDA receptor antagonists. Interestingly, in healthy volunteers, PCP-induced psychotomimetic action incorporates positive and negative symptoms as well as cognitive dysfunction, thus closely resembling schizophrenia in patients (Javitt D C et al., *Biol. Psychiatry,* 45: 668-679, 1999). Furthermore transgenic mice expressing reduced levels of the NMDAR1 subunit display behavioral abnormalities similar to those observed in pharmacologically induced models of schizophrenia, supporting a model in which reduced NMDA receptor activity results in schizophrenia-like behavior (Mohn A R et al., *Cell,* 98: 427-236, 1999).

Glutamate neurotransmission, in particular NMDA receptor activity, plays a critical role in synaptic plasticity, learning and memory, such that NMDA receptors appear to serve as a graded switch for gating the threshold of synaptic plasticity and memory formation (Wiley, N Y; Bliss T V and Collingridge G L, *Nature,* 361: 31-39, 1993). Transgenic mice overexpressing the NMDA NR2B subunit exhibit enhanced synaptic plasticity and superior ability in learning and memory (Tang J P et al., *Natur,* 401-63-69, 1999).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters act by removing neurotransmitters from the extracellular space, and can control their extracellular lifetime and thereby modulate the magnitude of the synaptic transmission (Gainetdinov R R et al, *Trends in Pharm. Sci.,* 23(8): 367-373, 2002).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., *Mol. Mem. Biol.,* 18: 13-20, 2001). Thus, one strategy to enhance NMDA receptor activity is to elevate the glycine concentration in the local microenvironment of synaptic NMDA receptors by inhibition of GlyT-1 transporter (Bergereon R. et al., *Proc. Natl. Acad. Sci. USA,* 95: 15730-15734, 1998; Chen L. et al., *J. Neurophysiol.,* 89(2): 691-703, 2003).

Glycine transporter inhibitors are suitable for the treatment of neurological and neuropsychiatric disorders. The majority of diseases states implicated are psychoses, schizophrenia (Armer R E and Miller D J, *Exp. Opin. Ther. Patents,* 11 (4): 563-572, 2001), psychotic mood disorders such as severe major depressive disorder, mood disorders associated with psychotic disorders such as acute mania or depression, associated with bipolar disorders and mood disorders, associated with schizophrenia, (Pralong E T et al., *Prog. Neurobiol.,* 67: 173-202, 2002), autistic disorders (Carlsson M L, *J. Neural Trans.* 105: 525-535, 1998), cognitive disorders such as dementias, including age related dementia and senile dementia of the Alzheimer type, memory disorders in a mammal, including a human, attention deficit disorders and pain (Armer R E and Miller D J, *Exp. Opin. Ther. Patents,* 11 (4): 563-572, 2001).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides compounds of formula I

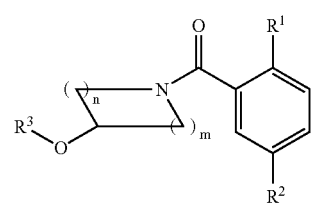

wherein
R$^1$ is —OR$^{1'}$, —SR$^{1'}$ or heterocycloalkyl group;
R$^{1'}$ is lower alkyl, lower alkyl substituted by halogen, or —(CH$_2$)$_n$-cycloalkyl;

R² is —S(O)₂-lower alkyl or —S(O)₂NH-lower alkyl;
R³ is aryl or heteroaryl, each of which is unsubstituted or substituted by one to three substituents, selected from the group consisting of lower alkyl, lower alkoxy, CN, NO₂, —C(O)-lower alkyl, —C(O)O-lower alkyl, halogen and lower alkyl substituted by halogen;
n is 1 or 2; and
m is 1 or 2;

and pharmaceutically acceptable acid addition salts thereof.

The invention includes all racemic mixtures, all their corresponding enantiomers and/or optical isomers. The present invention also provides pharmaceutical compositions containing compounds of the invention and a pharmaceutically acceptable carrier. The invention also provides methods for manufacturing compounds of the invention and compositions containing them.

Compounds of formula I are good inhibitors of the glycine transporter 1 (GlyT-1) and have a good selectivity to glycine transporter 2 (GlyT-2) inhibitors. The present invention further provides methods for the treatment of diseases related to activation of NMDA receptors via Glyt-1 inhibition, such as psychoses, dysfunction in memory and learning, schizophrenia, dementia and other diseases in which cognitive processes are impaired, such as attention deficit disorders or Alzheimer's disease. The preferred indications using the compounds of the present invention are schizophrenia, cognitive impairment and Alzheimer's disease.

The compounds of formula I can have the following structure:

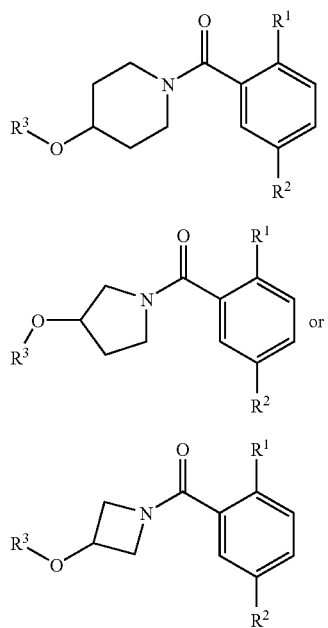

As used herein, the term "lower alkyl" denotes a saturated straight- or branched-carbon chain containing from 1 to 6 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "cycloalkyl" denotes a saturated ring containing from 3 to 6 carbon atoms.

As used herein, the term "lower alkoxy" denotes a saturated straight- or branched-carbon chain containing from 1 to 6 carbon atoms as described above, which is connected via an oxygen atom.

The term "halogen" denotes chlorine, iodine, fluorine and bromine.

The term "alkyl substituted by halogen" denotes an alkyl group as defined above, wherein at least one hydrogen atom is replaced by halogen, for example the following groups: $CF_3$, $CHF_2$, $CH_2F$, $CH_2CF_3$, $CH_2CHF_2$, $CH_2CH_2F$, $CH_2CH_2CF_3$, $CH_2CH_2CH_2CF_3$, $CH_2CH_2Cl$, $CH_2CF_2CF_3$, $CH_2CF_2CHF_2$, $CF_2CHFCF_3$, $C(CH_3)_2CF_3$, $CH(CH_3)CF_3$ or $CH(CH_2F)CH_2F$.

The term "aryl" denotes a monovalent cyclic aromatic hydrocarbon radical consisting of one or two fused rings in which at least one ring is aromatic in nature, for example phenyl, benzyl, naphthyl or biphenyl.

The term "heteroaryl" denotes a monovalent aromatic carbocyclic radical having one or two fused rings, which contains at least one heteroatom, for example pyridyl, pyrazinyl, pyrimidinyl, pyridazinyl or 1,3,5-triazinyl.

The term "heterocycloalkyl" denotes a non aromatic hydrocarbon radical having one or two fused rings, which contains at least one heteroatom for example oxetanyl, tetrahydrofuranyl, tetrahydropyranyl, azetidinyl, pyrrolidinyl, piperidinyl, piperazinyl, morpholinyl or thiomorpholinyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

The present invention provides compounds of formula I

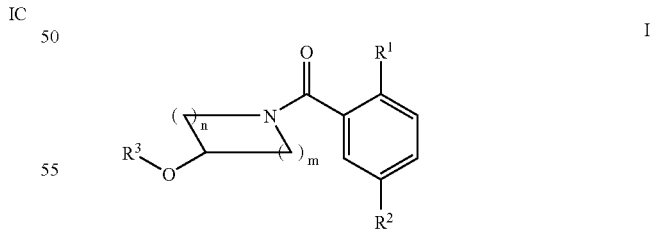

wherein
R¹ is —OR¹', —SR¹' or heterocycloalkyl group;
R¹' is lower alkyl, lower alkyl substituted by halogen, or —(CH₂)ₙ-cycloalkyl;
R² is —S(O)₂-lower alkyl or —S(O)₂NH-lower alkyl;
R³ is aryl or heteroaryl, each of which is unsubstituted or substituted by one to three substituents, selected from the group consisting of lower alkyl, lower alkoxy, CN, NO$_2$, —C(O)-lower alkyl, —C(O)O-lower alkyl, halogen and lower alkyl substituted by halogen;
n is 1 or 2; and
m is 1 or 2;

and pharmaceutically acceptable acid addition salts thereof.

In certain embodiments, the invention provides compounds of the following structures:

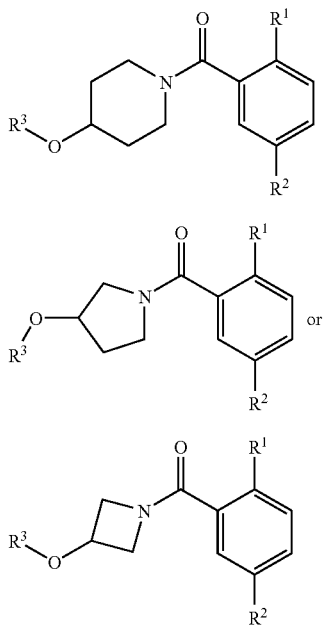

Furthermore, the invention includes all racemic mixtures, all their corresponding enantiomers and/or optical isomers.

Preferred compounds of the present application are compounds of formula I, wherein n and m are both 2. Such compounds of formula IA are (2-isopropoxy-5-methanesulfonyl-phenyl)-[4-(4-nitro-phenoxy)-piperidin-1-yl]-methanone, 1-{3-fluoro-4-[1-(2-isopropoxy-5-methanesulfonyl-benzoyl)-piperidin-4-yloxy]-phenyl}-ethanone and [4-(2-fluoro-5-trifluoromethyl-phenoxy)-piperidin-1-yl]-(2-isopropoxy-5-methanesulfonyl-phenyl)-methanone.

Further preferred are compounds of formula I, wherein n is 1 and m is 2, for example the following compounds of formula IB Rac-(2-isopropoxy-5-methanesulfonyl-phenyl)-[3-(4-trifluoromethyl-phenoxy)-pyrrolidin-1-yl]-methanone, Rac-(2-isopropoxy-5-methanesulfonyl-phenyl)-[3-(naphthalen-2-yloxy)-pyrrolidin-1-yl]-methanone, (5-methanesulfonyl-2-morpholin-4-yl-phenyl)-[3-(4-trifluoromethyl-phenoxy)-pyrrolidin-1-yl]-methanone and 4-cyclopentyloxy-N-methyl-3-[3-(4-trifluoromethyl-phenoxy)-pyrrolidine-1-carbonyl]-benzenesulfonamide.

Preferred compounds are further those, wherein n and m are both 1, for example the compounds of formula IC (2-isopropoxy-5-methanesulfonyl-phenyl)-[3-(4-trifluoromethyl-phenoxy)-azetidin-1-yl]-methanone, (2-isopropoxy-5-methanesulfonyl-phenyl)-[3-(3-trifluoromethyl-phenoxy)-azetidin-1-yl]-methanone, [5-methanesulfonyl-2-((S)-2,2,2-trifluoro-1-methyl-ethoxy)-phenyl]-[3-(4-trifluoromethyl-phenoxy)-azetidin-1-yl]-methanone and [5-methanesulfonyl-2-((R)-2,2,2-trifluoro-1-methyl-ethoxy)-phenyl]-[3-(4-trifluoromethyl-phenoxy)-azetidin-1-yl]-methanone.

In one embodiment, the invention provides compounds of formula I wherein R$^3$ is aryl which is unsubstituted or substituted by one to three substituents, selected from the group consisting of lower alkyl, lower alkoxy, CN, NO$_2$, —C(O)-lower alkyl, —C(O)O-lower alkyl, halogen and lower alkyl substituted by halogen. In particular, the invention provides compounds wherein R$^3$ is unsubstituted or substituted phenyl. The invention provides compounds wherein R$^3$ is unsubstituted phenyl. Alternatively, the invention provides compounds wherein R$^3$ is phenyl substituted by one to three substituents selected from the group consisting of NO$_2$, —C(O)-lower alkyl, and lower alkyl substituted by halogen. In particular, compound wherein R$^3$ is phenyl substituted by lower alkyl substituted by halogen are preferred, more particularly, those in which R$^3$ is phenyl substituted by trifluoromethyl.

In another embodiment, the invention provides compounds of formula I wherein R$^3$ is naphthyl which is unsubstituted or substituted by one to three substituents, selected from the group consisting of lower alkyl, lower alkoxy, CN, NO$_2$, —C(O)-lower alkyl, —C(O)O-lower alkyl, halogen and lower alkyl substituted by halogen.

In a further embodiment, the invention provides compounds of formula I wherein R$^3$ is heteroaryl which is unsubstituted or substituted by one to three substituents, selected from the group consisting of lower alkyl, lower alkoxy, CN, NO$_2$, —C(O)-lower alkyl, —C(O)O-lower alkyl, halogen and lower alkyl substituted by halogen.

In one embodiment, the present invention provides compounds of formula I in which R$^2$ is —S(O)$_2$-lower alkyl, in particular —S(O)$_2$-methyl.

In another embodiment, the invention provides compounds of formula I in which R$^1$ is OR$^{1'}$ or SR$^{1'}$. In particular, the invention provides compound in which R$^1$ is OR$^{1'}$, for example those in which R$^{1'}$ is lower alkyl. Alternatively, the invention provides compound of formula I wherein R$^1$ is OR$^{1'}$ and R$^{1'}$ is lower alkyl substituted by halogen.

In a further embodiment, the invention provides compounds of formula I in which R$^1$ is heterocycloalkyl.

The present compounds of formula I and their pharmaceutically acceptable salts can be prepared by methods known in the art, for example, by processes (a)-(c) described below, which process comprises a) reacting a compound of formula

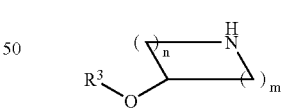

with a compound of formula

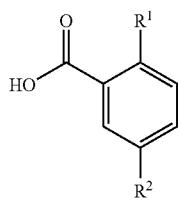

in the presence of an activating agent, such as TBTU (2-(1H-benzotriazole-1-yl)-1,1,3,3-tetramethyluroniumtetrafluoroborate), to produce a compound of formula

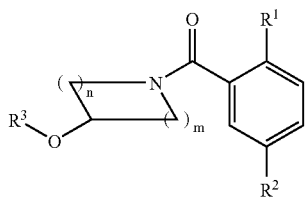

I wherein the substituents $R^1$, $R^2$ and $R^3$ are as defined above, and m and n are independently from each other 1 or 2;

b) reacting a compound of formula

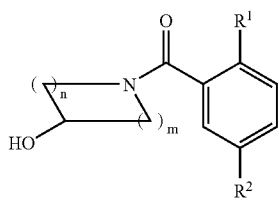

IV with a compound of formula

under Mitsunobu conditions in the present of a phosphine to produce a compound of formula

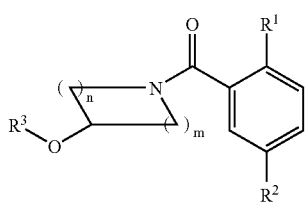

I wherein the substituents $R^1$, $R^2$ and $R^3$ are as defined above, and m and n are independently from each other 1 or 2;

c) reacting a compound of formula

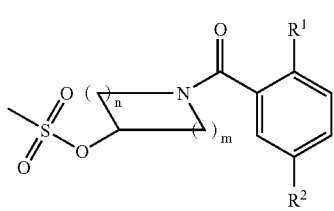

V with a compound of formula

in the presence of a base, such as sodium hydride, to produce a compound of formula

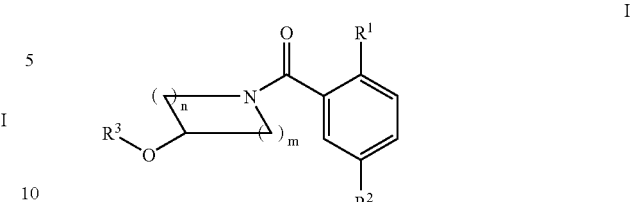

I wherein the substituents $R^1$, $R^2$ and $R^3$ are as defined above, and m and n are independently from each other 1 or 2;

and if desired, converting the compounds obtained into pharmaceutically acceptable acid addition salts.

The compounds of formula I can be prepared in accordance with process variants (a)-(c) and with the following schemes 1-6. The starting materials are either commercially available, are otherwise known in the chemical literature, or can be prepared in accordance with methods well known in the art.

Scheme 1

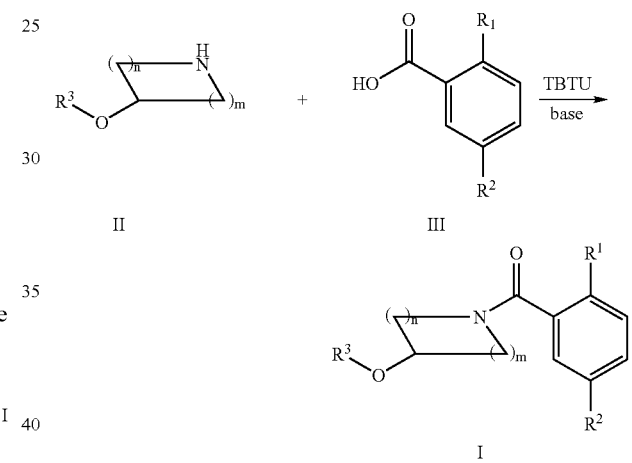

II      III

I

Compounds of general formula I can be prepared by reacting amine derivatives of formula II with an appropriately substituted acid of formula III in the presence of an activating agent, like TBTU (2-(1H-benzotriazole-1-yl)-1,1,3,3-tetramethyluroniumtetrafluoroborate), and a base, such as N-ethyldiisopropylamine (Scheme 1).

The amine compounds of formula II are either commercially available, are otherwise known in the chemical literature, or can be prepared using a variety of methods well known in the art.

The acids of formula III can be prepared by various routes as shown in Schemes 2-5.

Scheme 2

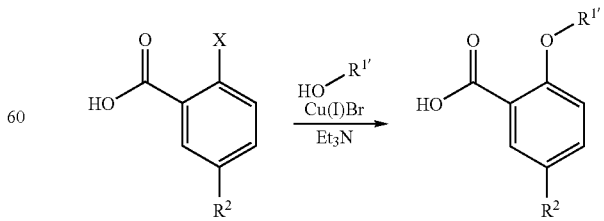

where X = halogen

VI      III

For example, compounds of formula III where $R^{1'}$ is lower alkyl, lower alkyl substituted by halogen or —$(CH_2)_n$-cycloalkyl can be prepared by reaction of a halogen compound of formula VI with an alcohol of formula $R^{1'}OH$, optionally in the presence of a copper salt, like Cu(I)Br, and a base, such as triethylamine (Scheme 2), at elevated temperature.

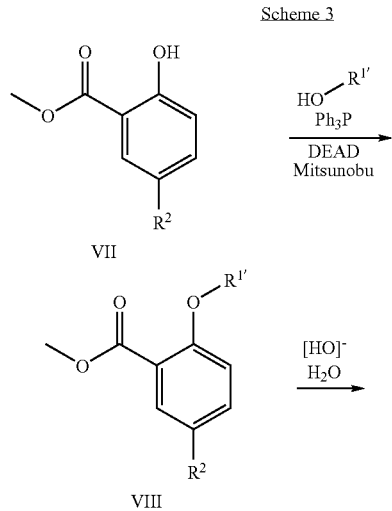

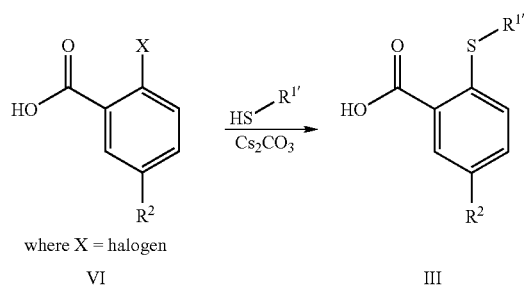

Compounds of formula III where $R^{1'}$ is lower alkyl, lower alkyl substituted by halogen or —$(CH_2)_n$-cycloalkyl can be prepared by reaction of a halogen compound of formula VI with a thiol of formula $R^{1'}SH$, optionally in the presence of a base, such as caesium carbonate, potassium carbonate or sodium carbonate (Scheme 4), at elevated temperature.

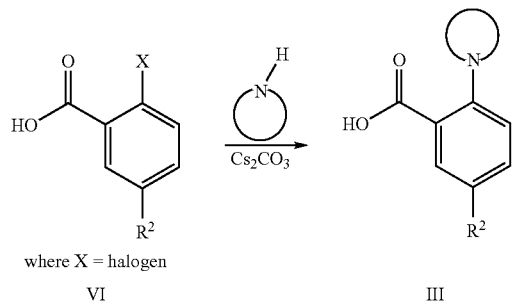

Alternatively, compounds of formula III where $R^{1'}$ is lower alkyl, lower alkyl substituted by halogen or —$(CH_2)_n$-cycloalkyl can be prepared by reacting a hydroxy compound of formula VII with an alcohol of formula $R^{1'}OH$, under Mitsunobu reaction conditions in the presence of a phosphine, like triphenylphosphine or diphenyl-2-pyridylphosphine, and a dialkylazadicarboxylate, like diethylazadicarboxylate or di-tert-butyl azodicarboxylate, to afford intermediate compounds of formula VIII, followed by hydrolysis in the presence of an aqueous base, such as potassium hydroxide, sodium hydroxide or lithium hydroxide (Scheme 3).

Compounds of formula III where $R^1$ is a heterocycloalkyl group, containing a N atom can be prepared by reaction of a halogen compound of formula VI with an amine of formula $R^{1'}R^{1''}NH$, optionally in the presence of a base, such as caesium carbonate, potassium carbonate or sodium carbonate (Scheme 5), at elevated temperature.

The halogen-substituted and hydroxy-substituted starting materials of formula VI and VII (as shown in Schemes 2-5) are either commercially available, are otherwise known in the chemical literature, or can be prepared using a variety of methods well known in the art.

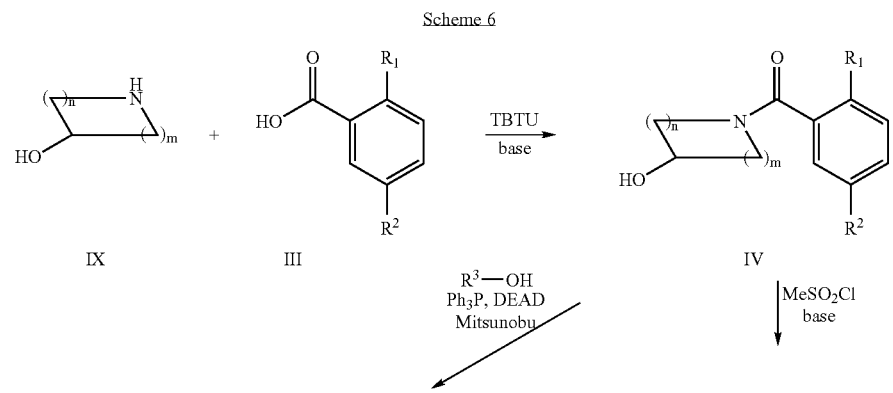

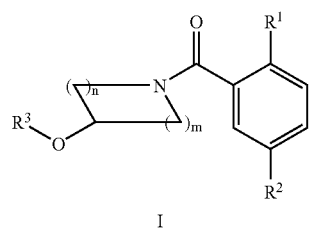 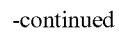 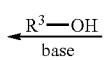 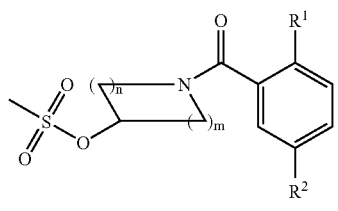

Compounds of general formula I can also be prepared by alternative routes as shown in Scheme 6. For instance, compounds of formula I can be prepared by reacting a hydroxy compound of formula IV with an alcohol of formula $R^3$—OH, under Mitsunobu reaction conditions in the presence of a phosphine, like triphenylphosphine or diphenyl-2-pyridylphosphine, and a dialkylazadicarboxylate, like diethylazadicarboxylate or di-tert-butyl azodicarboxylate. The compounds of formula IV can be prepared by reacting amines of formula IX with an appropriately substituted acid of formula III in the presence of an activating agent, like TBTU (2-(1H-benzotriazole-1-yl)-1,1,3,3-tetramethyluroniumtetrafluoroborate), and a base, such as N-ethyldiisopropylamine.

Compounds of formula I can also be prepared by reacting a hydroxy compound of formula IV with an alky- or arylsulphonyl chloride, e.g. methylsulfonyl chloride or p-toluenesulphonyl chloride, in the presence of a base, such as triethylamine or ethyldiisopropylamine, to afford intermediate compounds of formula V, which can then be reacted with an alcohol of formula $R^3$—OH in the presence of a base, such as sodium hydride, to afford the compounds of formula I.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I can be basic, for example in cases where the residue $R^3$ contains a basic group such as an aliphatic or aromatic amine moiety. In such cases the compounds of formula I can be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, compounds of the present invention are good inhibitors of the glycine transporter 1 (GlyT-1).

The compounds were investigated in accordance with the test given hereinafter.

Solutions and Materials

DMEM complete medium: Nutrient mixture F-12 (Gibco Life-technologies), fetal bovine serum (FBS) 5%, (Gibco life technologies), Penicillin/Streptomycin1% (Gibco life technologies), Hygromycin 0.6 mg/ml (Gibco life technologies), Glutamine 1 mM Gibco life technologies)

Uptake buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose. Flp-in™-CHO (Invitrogen Cat n° R758-07) cells stably transfected with mGlyT1b cDNA.

Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated, and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11-16 Ci/mmol) and 25 μM non-radioactive glycine. The plates were incubated with gentle shaking, and the reaction was stopped by aspiration of the mixture and washing (three times) with ice-cold UB. The cells were lysed with scintillation liquid, shaken 3 hours and the radioactivity in the cells was counted using a scintillation counter.

The preferred compounds show an IC$_{50}$ (µM) at GlyT-1 in the range of 0.07-1.00. Representative values are shown in the table below.

| Example No. | IC$_{50}$ (µM) | Example No. | IC$_{50}$ (µM) | Example No. | IC$_{50}$ (µM) |
|---|---|---|---|---|---|
| 4 | 1.00 | 18 | 0.87 | 24 | 0.84 |
| 5 | 0.93 | 21 | 0.87 | 25 | 0.078 |
| 8 | 0.63 | 22 | 0.70 | 26 | 0.109 |
| 13 | 0.55 | 23 | 0.39 | | |

The present invention also provides pharmaceutical compositions containing compounds of the invention, for example compounds of formula I and their pharmaceutically acceptable acid addition salts, and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions, moreover, can contain preservatives, solubilizers, stablizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers. Compounds of formula I are good inhibitors of the glycine transporter 1 (GlyT-1), and have good selectivity to glycine transporter 2 (GlyT-2) inhibitors. The invention further provides methods for the treatment of diseases related to activation of NMDA receptors via Glyt-1 inhibition, such as psychoses, dysfunction in memory and learning, schizophrenia, dementia and other diseases in which cognitive processes are impaired, such as attention deficit disorders or Alzheimer's disease. In particular, the present invention provides a method for treating schizophrenia, which comprises administering a therapeutically effective amount of a compound of formula I or a pharmaceutically acceptable salt thereof. The invention also provides a method of treating cognitive impairment, which comprises administering a therapeutically effective amount of a compound of formula I or a pharmaceutically acceptable salt thereof. The invention further provides a method for the treatment of Alzheimer's disease, which comprises administering a therapeutically effective amount of a compound of formula I or a pharmaceutically acceptable salt thereof.

The dosage at which the compound can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The following examples illustrate the invention but are not intended to limit its scope. The following abbreviations were used in the examples:

n-Boc-piperazine: tert-Butyl 1-piperazinecarboxylate,

Oxone®: (potassium peroxymonosulfate) 2KHSO$_5$.KHSO$_4$.K$_2$SO$_4$,

TBTU: 2-(1H-benzotriazole-1-yl)-1,1,3,3-tetramethyluroniumtetrafluoroborate;

Synthesis of Intermediates of Formula II

Example A1

2-Isopropoxy-5-methanesulfonyl-benzoic acid (a) 2-Chloro-5-methanesulfonyl-benzoic acid

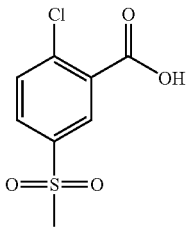

To 99 mmol 2-chloro-5-(methylthio)benzoic acid (purchased from Aldrich) in 400 ml methanol at 0° C. was added 296 mmol Oxone®, and the mixture was allowed to stir at RT for 3.5 h. The precipitate was filtered off, and the filtrate was concentrated under reduced pressure. The residue was extracted 3 times with 400 ml ethyl acetate, and the combined organic phases washed twice with 300 ml 1 N HCl and with 300 ml saturated aqueous NaCl solution and dried with MgSO$_4$. Evaporation under reduced pressure yielded the title compound which was used in the next step without further purification.

(b) 2-Isopropoxy-5-methanesulfonyl-benzoic acid

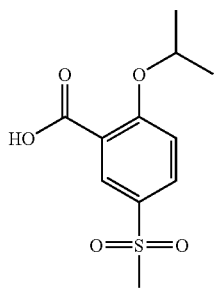

A mixture of 2.13 mmol 2-chloro-5-methanesulfonyl-benzoic acid, 0.64 mmol Cu(I)Br in 5 ml triethylamine and 25 ml isopropanol was heated to 120° C. for 16 h in a sealed tube. The volatiles were removed in vacuo, and the residue was taken up in 70 ml 1 N HCl. Extraction with ethyl acetate, drying of the combined organic fractions and evaporation yielded a residue which was purified by reversed phase preparative HPLC eluting with an acetonitrile/water gradient. Evaporation of the product fractions yielded the title compound. MS (m/e): 257.0 ([M−H]$^-$, 100%)

Example A2

5-Methanesulfonyl-2-((S)-2,2,2-trifluoro-1-methyl-ethoxy)-benzoic acid (a) rac-5-Methanesulfonyl-2-(2,2,2-trifluoro-1-methyl-ethoxy)-benzoic acid methyl ester

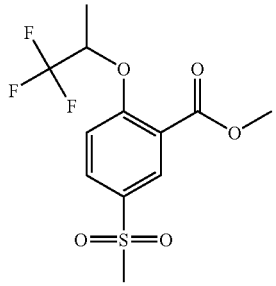

A mixture of 21.7 mmol 2-hydroxy-5-methanesulfonyl-benzoic acid methyl ester (WO 2002074774), 32.5 mmol trifluoro-methanesulfonic acid 2,2,2-trifluoro-1-methyl-ethyl ester [212556-43-9] and 43.4 mmol potassium carbonate in 87 ml DMF was stirred at 80° C. for 48 hours. After cooling to room temperature, the mixture was concentrated in vacuo, resuspended in water and stirred for 1 hour. Filtration yielded the title compound.

(b) 5-Methanesulfonyl-2-((S)-2,2,2-trifluoro-1-methyl-ethoxy)-benzoic acid methyl ester

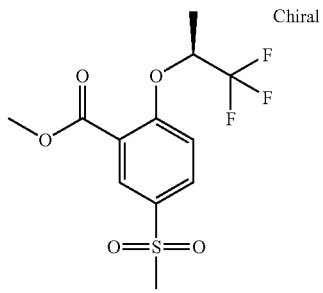

The title compound was obtained by separation of rac-5-methanesulfonyl-2-(2,2,2-trifluoro-1-methyl-ethoxy)-benzoic acid methyl ester by chiral HPLC (Chiralcel OD, 15% ethanol/heptane, flow 35 ml min$^{-1}$, 220 nm, retention time: 86 min.).

(c) 5-Methanesulfonyl-2-((S)-2,2,2-trifluoro-1-methyl-ethoxy)-benzoic acid

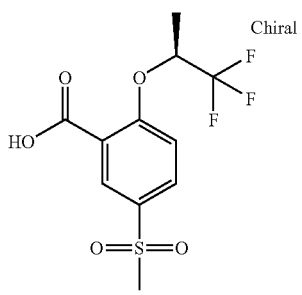

To 0.77 mmol 5-methanesulfonyl-2-((S)-2,2,2-trifluoro-1-methyl-ethoxy)-benzoic acid methyl ester in 2.5 ml ethanol was added 1.53 mmol 2 N aq NaOH solution, and the reaction mixture was stirred at 80° C. for 30 minutes. After such time the solvent was removed in vacuo, the residue was taken in water and acidified by addition of 2 N HCl. After filtration, the title compound was obtained as a white solid (92% yield). MS (m/e): 311.0 ([M−H]$^-$, 100%)

Example A3

5-Methanesulfonyl-2-((R)-2,2,2-trifluoro-1-methyl-ethoxy)-benzoic acid (a) 5-Methanesulfonyl-2-((R)-2,2,2-trifluoro-1-methyl-ethoxy)-benzoic acid methyl ester

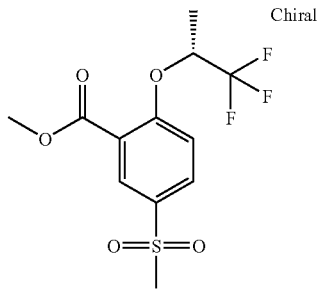

The title compound was obtained by separation of rac-5-methanesulfonyl-2-(2,2,2-trifluoro-1-methyl-ethoxy)-benzoic acid methyl ester (Example A2(a)) by chiral HPLC (Chiralcel OD, 15% ethanol/Heptane, flow 35 ml min⁻¹, 220 nm, retention time: 74 min.).

(b) 5-Methanesulfonyl-2-((R)-2,2,2-trifluoro-1-methyl-ethoxy)-benzoic acid

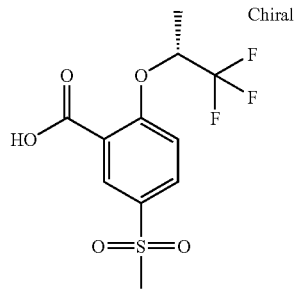

Prepared in analogy to Example A2(c) from 5-methanesulfonyl-2-((R)-2,2,2-trifluoro-1-methyl-ethoxy)-benzoic acid methyl ester. MS (m/e): 311.0 ([M−H]⁻¹, 100%)

Example A4

5-Methanesulfonyl-2-morpholin-4-yl-benzoic acid

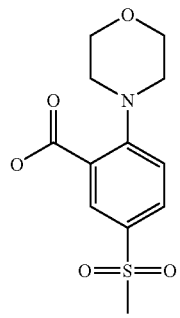

A mixture of 4.26 2-chloro-5-methanesulfonyl-benzoic acid (Example A1(a)) and 91.8 mmol morpholine was heated at 110° C. for 15 h with shaking. The volatiles were removed in vacuo, and the residue was acidified with 4 M aq HCl and then further diluted with 150 ml 1 N aq HCl. The mixture was extracted three times with ethyl acetate, and the combined organic phases washed with brine and then dried over magnesium sulfate. Evaporation in vacuo yielded the title compound as a light-yellow amorphous solid. MS (m/e): 284.0 ([M−H]⁻¹, 100%)

Example A5

2-Cyclopentyloxy-5-methylsulfamoyl-benzoic acid (a) 5-Chlorosulfonyl-2-hydroxy-benzoic acid

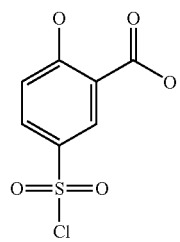

To 3.26 mol chlorosulfonic acid at 0° C. was added 652 mmol salicylic acid in small portions, and the mixture was then allowed to stir at RT for 1 h, then at 50° C. for 1 h, and finally at 70° C. for 1 h. The mixture was then added dropwise to 1000 ml ice-water with stirring and stirring continued for an additional 30 min. The ensuing white crystals were collected by filtration, washed three times with water, and then dried in vacuo at 45° C. for 16 h to yield the title compound. MS (m/e): 236.8 ([{³⁷Cl}M−H]⁻, 33%), 235.0 ([{³⁷Cl}M−H]⁻, 100%)

(b) 2-Hydroxy-5-methylsulfamoyl-benzoic acid

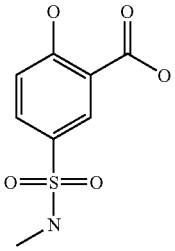

To 63 mmol 5-chlorosulfonyl-2-hydroxy-benzoic acid in 120 ml dichloromethane at RT was added dropwise 317 mmol methylamine (8 M solution in ethanol), and the mixture was allowed to stir at RT for 1 h. The mixture was then concentrated in vacuo. The residue was suspended in 1 M aq NaOH solution and extracted twice with ether. The aqueous phase was acidified with 5 M aq HCl, saturated with NaCl, and extracted 3 times with THF. The combined THF extracts were washed twice with saturated aqueous NaCl solution and dried with Na₂SO₄. Evaporation in vacuo yielded the title compound. MS (m/e): 249.0 (M+NH₄⁺, 100%), 231.9 (M+H⁺, 63%)

(c) 2-Hydroxy-5-methylsulfamoyl-benzoic acid methyl ester

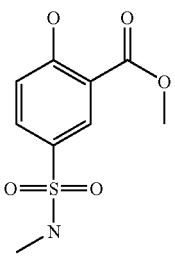

To 77 mmol 2-hydroxy-5-methylsulfamoyl-benzoic acid in 300 ml THF was added 85 mmol CDI, and the mixture heated at 70° C. for 1 h. 770 mmol methanol was then added and the mixture was heated at 70° C. for 16 h. The mixture was then cooled to room temperature and concentrated in vacuo. The residue was chromatographed on silica gel (eluant:ethyl acetate/heptane/dichloromethane 45:45:10) to afford the title compound. MS (m/e): 244.1 ([M−H]⁻, 100%)

(d) 2-Cyclopentyloxy-5-methylsulfamoyl-benzoic acid methyl ester

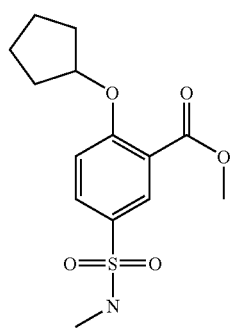

To 2.85 mmol 2-hydroxy-5-methylsulfamoyl-benzoic acid methyl ester, 3.14 mmol cyclopentanol and 3.28 mmol triphenylphosphine in 10 ml THF was added 3.14 mmol di-tert-butyl azodicarboxylate, and the mixture was stirred at RT for 2 h. The mixture was then concentrated in vacuo. The residue was chromatographed on silica gel (eluant:ethyl acetate/heptane 2:3) to afford the title compound as a colourless oil. MS (m/e): 312.1 ([M–H]⁻, 100%)

(e) 2-Cyclopentyloxy-5-methylsulfamoyl-benzoic acid

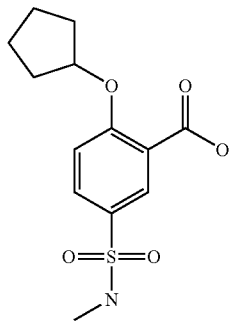

To 2.68 mmol 2-cyclopentyloxy-5-methylsulfamoyl-benzoic acid methyl ester in 10 ml THF was added 20 mmol 2 M aq NaOH, and the mixture was stirred at RT for 2 h. The mixture was then extracted twice with ether. The aqueous phase was acidified with 10% aq citric acid and extracted 3 times with ethyl acetate. The combined organic phases were dried with $Na_2SO_4$. Evaporation in vacuo followed by trituration in ether afforded the title compound as a white solid. MS (m/e): 298.3 ([M–H]⁻, 100%)

Example A6

2-Isopropylsulfanyl-5-methanesulfonyl-benzoic acid a) 2-Fluoro-5-methylsulfanyl-benzoic acid

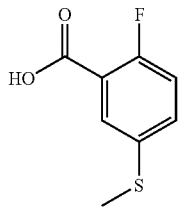

The title compound was prepared by following the procedure described in: Journal of Organometallic Chemistry 1991, 419(1-2), 1-8.

b) 2-Fluoro-5-methanesulfonyl-benzoic acid

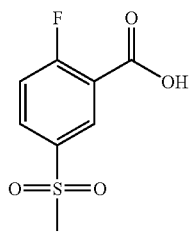

To 2.68 mmol 2-fluoro-5-methanesulfanyl-benzoic acid in 5 ml methanol at 0° C. was added 8.05 mmol Oxone®, and the mixture was allowed to stir at RT for 72 h. The precipitate was filtered off, and the filtrate was concentrated under reduced pressure. The residue was treated with water and extracted 3 times with 400 ml dichloromethane. The combined organic phases were dried over sodium sulfate. Evaporation under reduced pressure yielded the title compound as a white crystalline solid (yield 79%). MS (m/e): 217.2 (M–H⁺, 100%).

c) 2-Isopropylsulfanyl-5-methanesulfonyl-benzoic acid

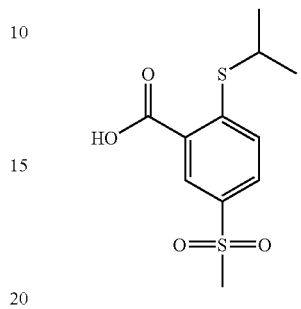

To a solution of 4.58 mmol 2-fluoro-5-methanesulfonyl-benzoic acid in 6 ml N,N-dimethylacetamide were added 15.2 mol cesium carbonate and 10.1 mmol 2-propanethiol, and the mixture was stirred at 90° C. for 3 h. The reaction mixture was then cooled to room temperature and acidified to pH 1 by addition of hydrochloric acid before being extracted three times with ethyl acetate. The combined organic phases were dried over sodium sulfate and concentrated in vacuo to afford the title compound as a light yellow liquid which was used in the next step without further purification (yield 99%). EI-MS (m/e): 274.1 (M⁺, 35%), 232.1 ([M-$C_3H_6$]⁺, 30%, 214.1 (M-$C_3H_6$—$H_2O$)⁺, 100%).

Synthesis of Compounds of Formula I

Example 1

(2-Isopropoxy-5-methanesulfonyl-phenyl)-[4-(pyridin-4-yloxy)-piperidin-1-yl]-methanone

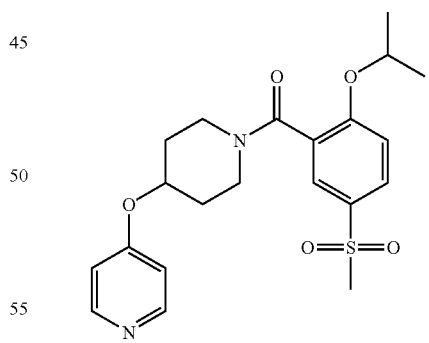

To a solution of 0.19 mmol 2-isopropoxy-5-methanesulfonyl-benzoic acid (Example A1) in 1 ml N,N-dimethylformamide were added successively 0.29 mmol TBTU, 0.97 mmol N-ethyldiisopropylamine and 0.19 mmol 4-(piperidin-4-yloxy)-pyridine. The reaction mixture was stirred at RT for 16 h and then concentrated in vacuo. Reversed phase HPLC (acetonitrile/water) afforded the title compound as amorphous white solid (yield 75%). MS (m/e): 419.2 (M+H⁺, 100%).

Example 2

(2-Isopropoxy-5-methanesulfonyl-phenyl)-[4-(4-methoxy-phenoxy)-piperidin-1-yl]-methanone

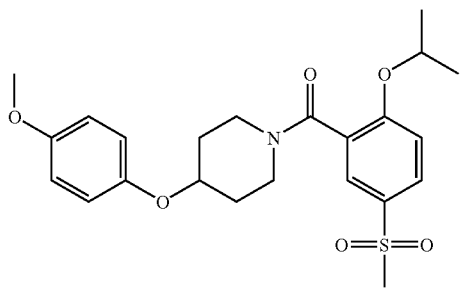

Prepared in analogy to Example 1 from 2-isopropoxy-5-methanesulfonyl-benzoic acid (Example A1) and 4-(4-methoxy-phenoxy)-piperidine. The crude material was purified by reversed phase HPLC (acetonitrile/water) to yield the title compound as an amorphous white solid (yield 73%). MS (m/e): 448.2 (M+H$^+$, 100%).

Example 3

4-[1-(2-Isopropoxy-5-methanesulfonyl-benzoyl)-piperidin-4-yloxy]-benzonitrile a) (4-Hydroxy-piperidin-1-yl)-(2-isopropoxy-5-methanesulfonyl-phenyl)-methanone

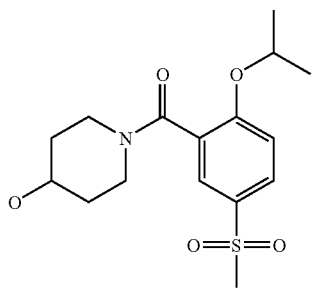

Prepared in analogy to Example 1 from 2-isopropoxy-5-methanesulfonyl-benzoic acid (Example A1) and 4-hydroxypiperidine. The crude material was purified by flash chromatography (methanol/dichloromethane) to yield the title compound as an amorphous yellow solid (yield 70%). MS (m/e): 342.3 (M+H$^+$, 100%).

b) Methanesulfonic acid 1-(2-isopropoxy-5-methanesulfonyl-benzoyl)-piperidin-4-yl ester

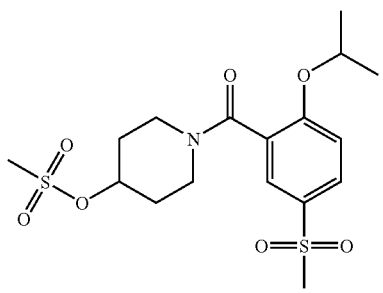

To a solution of 0.29 mmol (4-hydroxy-piperidin-1-yl)-(2-isopropoxy-5-methanesulfonyl-phenyl)-methanone in 6 ml dichloromethane at 0° C. were added successively 0.73 mmol triethylamine and 0.35 mmol methanesulfonyl chloride. The reaction mixture was stirred at 0° C. for 20 min and then at RT for 2 h. The reaction mixture was then diluted with dichloromethane, washed with water, and the organic phase dried over sodium sulfate and concentrated in vacuo to afford the title compound as a light brown solid (yield 93%). MS (m/e): 420.1 (M+H$^+$, 100%).

c) 4-[1-(2-Isopropoxy-5-methanesulfonyl-benzoyl)-piperidin-4-yloxy]-benzonitrile

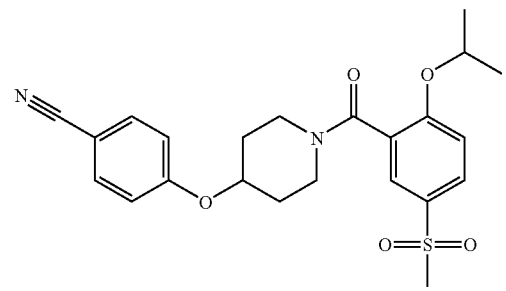

To a solution of 0.14 mmol 4-cyanophenol in 1 ml N,N-dimethylformamide was added 0.19 mmol sodium hydride (60% suspension in oil) and the mixture was stirred at room temperature for 30 min. 0.12 mmol methanesulfonic acid 1-(2-isopropoxy-5-methanesulfonyl-benzoyl)-piperidin-4-yl ester was then added, and the reaction mixture was stirred at 60° C. for 2 h and then at 80° C. for 3 h. The reaction mixture was then cooled to room temperature and concentrated in vacuo. The crude material was purified by reversed phase HPLC (acetonitrile/water) to afford the title compound as a white crystalline solid (yield 21%). MS (m/e): 443.4 (M+H$^+$, 100%).

Example 4

(2-Isopropoxy-5-methanesulfonyl-phenyl)-[4-(4-nitro-phenoxy)-piperidin-1-yl]-methanone

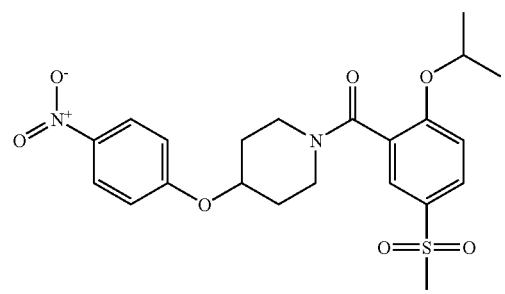

To a solution of 0.15 mmol (4-hydroxy-piperidin-1-yl)-(2-isopropoxy-5-methanesulfonyl-phenyl)-methanone (Example 3(a)) in 3 ml tetrahydrofuran were added successively 0.18 mmol 4-nitrophenol, 0.18 mmol triphenylphosphine and 0.18 mmol di-tert-butyl azodicarboxylate. The reaction mixture was stirred at 50° C. for 16 h and was then cooled to room temperature and concentrated in vacuo. The crude material was purified by reversed phase HPLC (acetonitrile/water) to afford the title compound as a white crystalline solid (yield 27%). MS (m/e): 463.4 (M+H$^+$, 100%).

Example 5

1-{3-Fluoro-4-[1-(2-isopropoxy-5-methanesulfonyl-benzoyl)-piperidin-4-yloxy]-phenyl}-ethanone

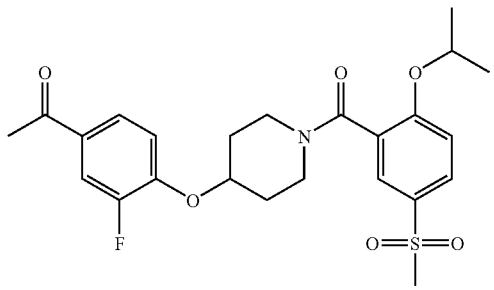

Prepared in analogy to Example 4 from (4-hydroxy-piperidin-1-yl)-(2-isopropoxy-5-methanesulfonyl-phenyl)-methanone (Example 3(a)) and 3-fluoro-4-hydroxyacetophenone. The crude material was purified by reversed phase HPLC (acetonitrile/water) to yield the title compound as an amorphous white solid (yield 21%). MS (m/e): 478.4 (M+H$^+$, 100%).

Example 6

[4-(2,4-Difluoro-phenoxy)-piperidin-1-yl]-(2-isopropoxy-5-methanesulfonyl-phenyl)-methanone

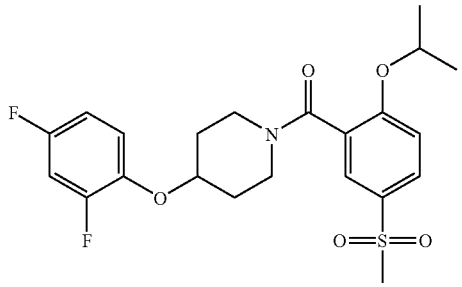

Prepared in analogy to Example 4 from (4-hydroxy-piperidin-1-yl)-(2-isopropoxy-5-methanesulfonyl-phenyl)-methanone (Example 3(a)) and 2,4-difluorophenol. The crude material was purified by reversed phase HPLC (acetonitrile/water) to yield the title compound as an amorphous white solid (yield 21%). MS (m/e): 454.3 (M+H$^+$, 100%).

Example 7

4-[1-(2-Isopropoxy-5-methanesulfonyl-benzoyl)-piperidin-4-yloxy]-benzoic acid ethyl ester

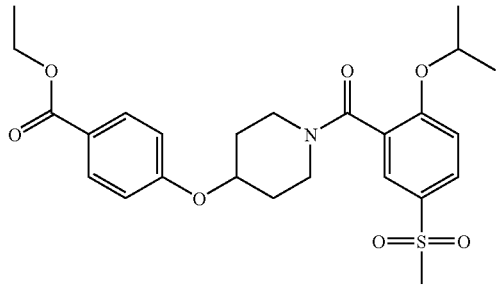

Prepared in analogy to Example 4 from (4-hydroxy-piperidin-1-yl)-(2-isopropoxy-5-methanesulfonyl-phenyl)-methanone (Example 3(a)) and ethyl 4-hydroxybenzoate. The crude material was purified by reversed phase HPLC (acetonitrile/water) to yield the title compound as an amorphous white solid (yield 28%). MS (m/e): 490.5 (M+H$^+$, 100%).

Example 8

[4-(2-Fluoro-5-trifluoromethyl-phenoxy)-piperidin-1-yl]-(2-isopropoxy-5-methanesulfonyl-phenyl)-methanone

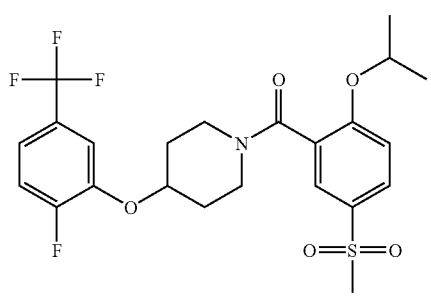

Prepared in analogy to Example 4 from (4-hydroxy-piperidin-1-yl)-(2-isopropoxy-5-methanesulfonyl-phenyl)-methanone (Example 3(a)) and 2-fluoro-5-(trifluoromethyl)phenol. The crude material was purified by reversed phase HPLC (acetonitrile/water) to yield the title compound as an amorphous white solid (yield 35%). MS (m/e): 504.4 (M+H$^+$, 100%).

Example 9

Rac-1-{3,5-Difluoro-4-[1-(2-isopropoxy-5-methanesulfonyl-benzoyl)-pyrrolidin-3-yloxy]-phenyl}-propan-1-one a) rac-(3-Hydroxy-pyrrolidin-1-yl)-(2-isopropoxy-5-methanesulfonyl-phenyl)-methanone

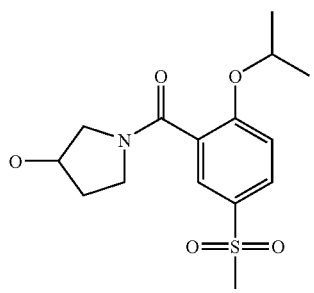

Prepared in analogy to Example 1 from 2-isopropoxy-5-methanesulfonyl-benzoic acid (Example A1) and rac-3-pyrrolidinol. The crude material was purified by flash chromatography (methanol/dichloromethane) to yield the title compound as a light brown foam (yield 50%). MS (m/e): 328.1 (M+H$^+$, 100%).

b) rac-1-{3,5-Difluoro-4-[1-(2-isopropoxy-5-methanesulfonyl-benzoyl)-pyrrolidin-3-yloxy]-phenyl}-propan-1-one

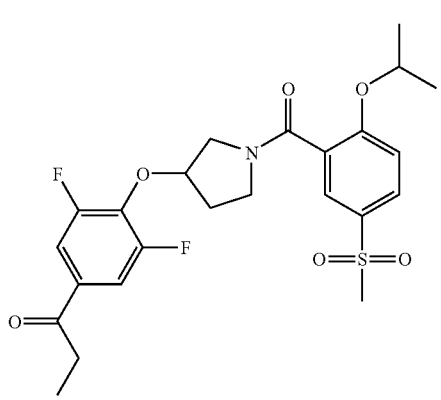

Prepared in analogy to Example 4 from rac-(3-hydroxy-pyrrolidin-1-yl)-(2-isopropoxy-5-methanesulfonyl-phenyl)-methanone and 3,5-difluoro-4-hydroxypropiophenone. The crude material was purified by reversed phase HPLC (acetonitrile/water) to yield the title compound as an amorphous white solid (yield 21%). MS (m/e): 496.5 (M+H$^+$, 100%).

Example 10

Rac-[3-(2-Fluoro-5-trifluoromethyl-phenoxy)-pyrrolidin-1-yl]-(2-isopropoxy-5-methanesulfonyl-phenyl)-methanone

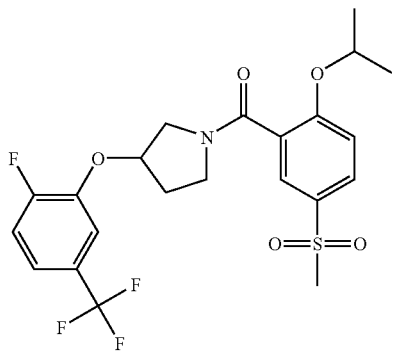

Prepared in analogy to Example 4 from rac-(3-hydroxy-pyrrolidin-1-yl)-(2-isopropoxy-5-methanesulfonyl-phenyl)-methanone (Example 9(a)) and 2-fluoro-5-(trifluoromethyl)phenol. The crude material was purified by reversed phase HPLC (acetonitrile/water) to yield the title compound as an amorphous white solid (yield 25%). MS (m/e): 490.4 (M+H$^+$, 100%).

Example 11

Rac-(2-Isopropoxy-5-methanesulfonyl-phenyl)-[3-(4-nitro-phenoxy)-pyrrolidin-1-yl]-methanone

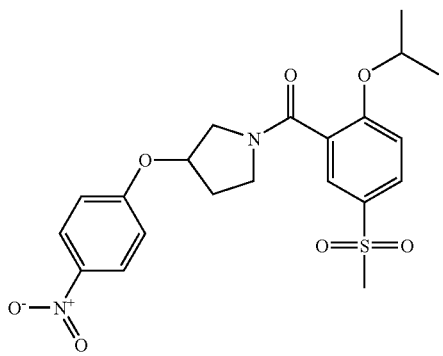

Prepared in analogy to Example 4 from rac-(3-hydroxy-pyrrolidin-1-yl)-(2-isopropoxy-5-methanesulfonyl-phenyl)-methanone (Example 9(a)) and 4-nitrophenol. The crude material was purified by reversed phase HPLC (acetonitrile/water) to yield the title compound as an amorphous white solid (yield 25%). MS (m/e): 449.3 (M+H$^+$, 100%).

Example 12

Rac-[3-(2-Fluoro-4-nitro-phenoxy)-pyrrolidin-1-yl]-(2-isopropoxy-5-methanesulfonyl-phenyl)-methanone

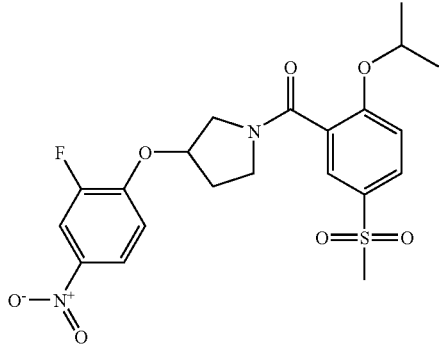

Prepared in analogy to Example 4 from rac-(3-hydroxy-pyrrolidin-1-yl)-(2-isopropoxy-5-methanesulfonyl-phenyl)-methanone (Example 9(a)) and 2-fluoro-4-nitrophenol. The crude material was purified by reversed phase HPLC (acetonitrile/water) to yield the title compound as an amorphous white solid (yield 23%). MS (m/e): 467.4 (M+H$^+$, 100%).

Example 13

Rac-(2-Isopropoxy-5-methanesulfonyl-phenyl)-[3-(4-trifluoromethyl-phenoxy)-pyrrolidin-1-yl]-methanone

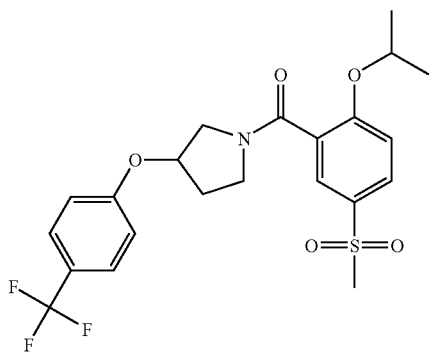

Prepared in analogy to Example 4 from rac-(3-hydroxy-pyrrolidin-1-yl)-(2-isopropoxy-5-methanesulfonyl-phenyl)-methanone (Example 9(a)) and 4-hydroxybenzotrifluoride. The crude material was purified by reversed phase HPLC (acetonitrile/water) to yield the title compound as an amorphous white solid (yield 28%). MS (m/e): 472.4 (M+H$^+$, 100%).

Example 14

Rac-1-{3-Fluoro-4-[1-(2-isopropoxy-5-methane-sulfonyl-benzoyl)-pyrrolidin-3-yloxy]-phenyl}-ethanone a) Rac-Methanesulfonic acid 1-(2-isopropoxy-5-methanesulfonyl-benzoyl)-pyrrolidin-3-yl ester

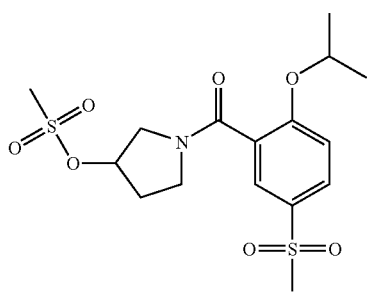

Prepared in analogy to Example 3(b) from rac-(3-hydroxy-pyrrolidin-1-yl)-(2-isopropoxy-5-methanesulfonyl-phenyl)-methanone (Example 9(a)) and methanesulfonyl chloride. The crude material was purified by partitioning between dichoromethane and water to yield the title compound as a yellow oil (yield 99%). MS (m/e): 406.4 (M+H$^+$, 100%).

b) rac-1-{3-Fluoro-4-[1-(2-isopropoxy-5-methane-sulfonyl-benzoyl)-pyrrolidin-3-yloxy]-phenyl}-ethanone

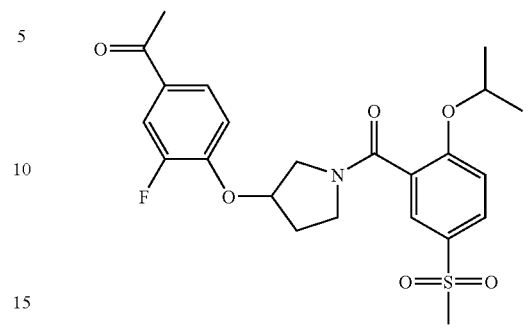

Prepared in analogy to Example 3(c) from rac-methanesulfonic acid 1-(2-isopropoxy-5-methanesulfonyl-benzoyl)-pyrrolidin-3-yl ester (Example 14(a)) and 3-fluoro-4-hydroxyacetophenone. The crude material was purified by reversed phase HPLC (acetonitrile/water) to yield the title compound as an amorphous white solid (yield 62%). MS (m/e): 464.0 (M+H$^+$, 100%).

Example 15

Rac-(2-Isopropoxy-5-methanesulfonyl-phenyl)-[3-(3-trifluoromethyl-phenoxy)-pyrrolidin-1-yl]-methanone

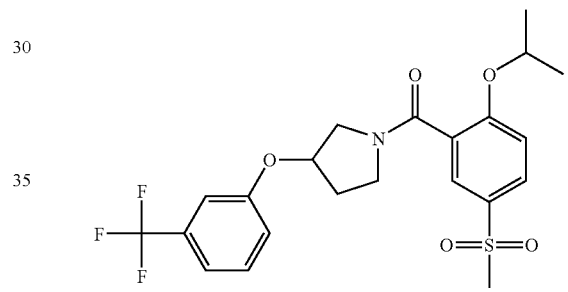

Prepared in analogy to Example 3(c) from rac-methanesulfonic acid 1-(2-isopropoxy-5-methanesulfonyl-benzoyl)-pyrrolidin-3-yl ester (Example 14(a)) and 3-hydroxybenzotrifluoride. The crude material was purified by reversed phase HPLC (acetonitrile/water) to yield the title compound as an amorphous white solid (yield 45%). MS (m/e): 472.4 (M+H$^+$, 100%).

Example 16

Rac-[3-(3,5-Bis-trifluoromethyl-phenoxy)-pyrrolidin-1-yl]-(2-isopropoxy-5-methanesulfonyl-phenyl)-methanone

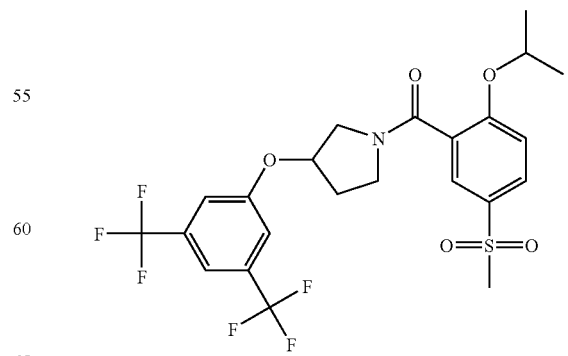

Prepared in analogy to Example 3(c) from rac-methanesulfonic acid 1-(2-isopropoxy-5-methanesulfonyl-benzoyl)- pyrrolidin-3-yl ester (Example 14(a)) and 3,5-bis(trifluoromethyl)phenol. The crude material was purified by reversed phase HPLC (acetonitrile/water) to yield the title compound as an amorphous white solid (yield 19%). MS (m/e): 540.3 (M+H+, 100%).

Example 17

Rac-[3-(3,4-Dichloro-phenoxy)-pyrrolidin-1-yl]-(2-isopropoxy-5-methanesulfonyl-phenyl)-methanone

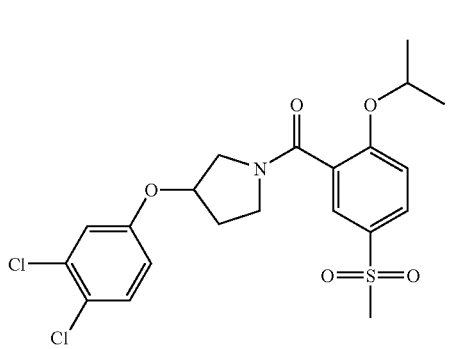

Prepared in analogy to Example 3(c) from rac-methanesulfonic acid 1-(2-isopropoxy-5-methanesulfonyl-benzoyl)-pyrrolidin-3-yl ester (Example 14(a)) and 3,4-dichlorophenol. The crude material was purified by reversed phase HPLC (acetonitrile/water) to yield the title compound as an amorphous white solid (yield 32%). MS (m/e): 476.3 ({$^{37}$Cl}M+H+, 10%), 474.3 ({$^{37}$C,$^{35}$Cl}M+H+, 80%), 472.2 ({$^{35}$Cl}M+H+, 100%)

Example 18

Rac-(2-Isopropoxy-5-methanesulfonyl-phenyl)-[3-(naphthalen-2-yloxy)-pyrrolidin-1-yl]-methanone

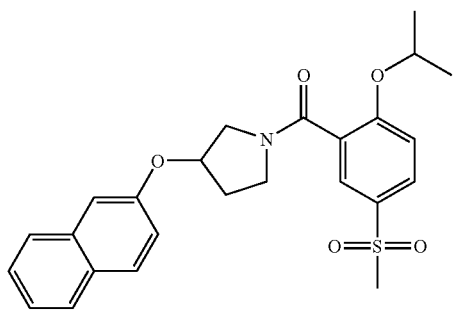

Prepared in analogy to Example 3(c) from rac-methanesulfonic acid 1-(2-isopropoxy-5-methanesulfonyl-benzoyl)-pyrrolidin-3-yl ester (Example 14(a)) and 2-naphthol. The crude material was purified by reversed phase HPLC (acetonitrile/water) to yield the title compound as an amorphous yellow solid (yield 40%). MS (m/e): 454.5 (M+H+, 100%).

Example 19

Rac-(2-Isopropoxy-5-methanesulfonyl-phenyl)-[3-(4-nitro-3-trifluoromethyl-phenoxy)-pyrrolidin-1-yl]-methanone

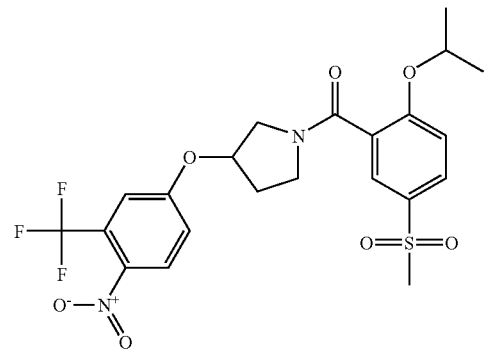

Prepared in analogy to Example 4 from rac-(3-hydroxy-pyrrolidin-1-yl)-(2-isopropoxy-5-methanesulfonyl-phenyl)-methanone (Example 9(a)) and 5-hydroxy-2-nitrobenzotrifluoride. The crude material was purified by reversed phase HPLC (acetonitrile/water) to yield the title compound as an amorphous white solid (yield 56%). MS (m/e): 517.5 (M+H+, 100%).

Example 20

Rac-[3-(3-Fluoro-5-trifluoromethyl-phenoxy)-pyrrolidin-1-yl]-(2-isopropoxy-5-methanesulfonyl-phenyl)-methanone

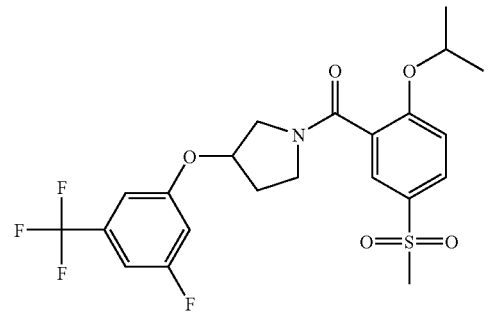

Prepared in analogy to Example 4 from rac-(3-hydroxy-pyrrolidin-1-yl)-(2-isopropoxy-5-methanesulfonyl-phenyl)-methanone (Example 9(a)) and 3-fluoro-5-(trifluoromethyl) phenol. The crude material was purified by reversed phase HPLC (acetonitrile/water) to yield the title compound as an amorphous white solid (yield 45%). MS (m/e): 490.1 (M+H+, 100%).

Example 21

(2-Isopropoxy-5-methanesulfonyl-phenyl)-[3-(4-trifluoromethyl-phenoxy)-azetidin-1-yl]-methanone a) (3-Hydroxy-azetidin-1-yl)-(2-isopropoxy-5-methanesulfonyl-phenyl)-methanone

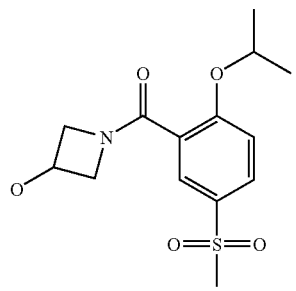

Prepared in analogy to Example 1 from 2-isopropoxy-5-methanesulfonyl-benzoic acid (Example A1) and azetin-3-ol. The crude material was purified by flash chromatography (methanol/dichloromethane) to yield the title compound as a pink solid (yield 62%). MS (m/e): 314.0 (M+H$^+$, 100%).

b) (2-Isopropoxy-5-methanesulfonyl-phenyl)-[3-(4-trifluoromethyl-phenoxy)-azetidin-1-yl]-methanone

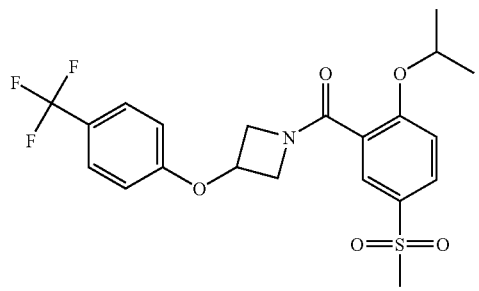

A mixture of 0.32 mmol (3-hydroxy-azetidin-1-yl)-(2-isopropoxy-5-methanesulfonyl-phenyl)-methanone, 0.32 mmol 4-fluoro-benzotrifluoride and 0.96 mmol cesium carbonate in 10 ml acetonitrile was refluxed overnight. The reaction mixture was concentrated to yield the crude compound, purified by chromatography (methanol/dichloromethane). MS (m/e): 458.4 (M+H$^+$, 100%).

Example 22

(2-Isopropoxy-5-methanesulfonyl-phenyl)-[3-(3-trifluoromethyl-phenoxy)-azetidin-1-yl]-methanone a) 1-Benzhydryl-3-(3-trifluoromethyl-phenoxy)-azetidine

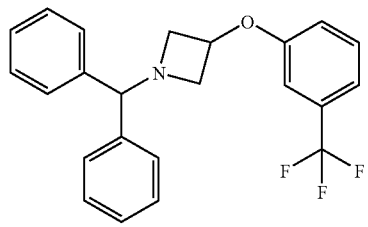

A suspension of 1 mmol methanesulfonic acid 1-benzhydryl-azetidin-3-yl ester [33301-41-6], 1 mmol 3-hydroxy benzotrifluoride, 0.05 mmol tetrabutyl ammonium bromide and 4 mmol sodium hydroxide in a mixture of 5 ml toluene and 0.2 ml water was refluxed overnight. The reaction mixture was cooled, diluted with 20 ml of water and extracted 3 times with dichloromethane. The organic phase was dried, concentrated and the crude product purified by chromatography (methanol/dichloromethane). MS (m/e): 442.3 ([M+CH$_3$COO$^-$]$^-$, 100%).

b) 3-(3-Trifluoromethyl-phenoxy)-azetidine

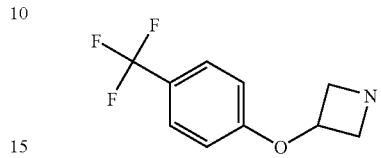

44 mg of 10% palladium on charcoal was added to a solution of 0.23 mmol 1-benzhydryl-3-(3-trifluoromethyl-phenoxy)-azetidine in 5 ml acetic acid. The reaction mixture was hydrogenated for 3 hours at room temperature and normal pressure. Filtration and concentration yielded the crude product which was used in the next step without further purification. MS (m/e): 218.2 (M+H$^+$, 100%).

c) (2-Isopropoxy-5-methanesulfonyl-phenyl)-[3-(3-trifluoromethyl-phenoxy)-azetidin-1-yl]-methanone

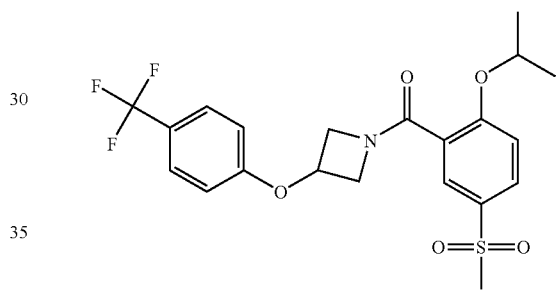

Prepared in analogy to Example 1 from 2-isopropoxy-5-methanesulfonyl-benzoic acid (Example A1) and 3-(3-trifluoromethyl-phenoxy)-azetidine. The crude material was purified by chromatography (methanol/dichloromethane) to yield the title compound as an amorphous white solid (yield 7%). MS (m/e): 458.2 (M+H$^+$, 100%).

Example 23

[5-Methanesulfonyl-2-((S)-2,2,2-trifluoro-1-methyl-ethoxy)-phenyl]-[3-(4-trifluoromethyl-phenoxy)-azetidin-1-yl]-methanone a) (3-Hydroxy-azetidin-1-yl)-[5-methanesulfonyl-2-((S)-2,2,2-trifluoro-1-methyl-ethoxy)-phenyl]-methanone

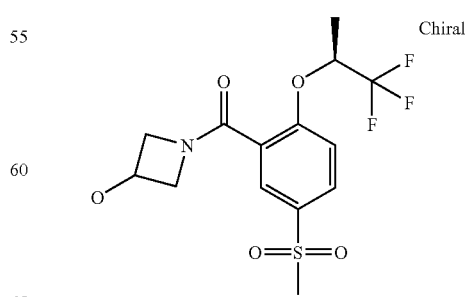

Prepared in analogy to Example 1 from 5-methanesulfonyl-2-((S)-2,2,2-trifluoro-1-methyl-ethoxy)-benzoic acid (Example A2(c)) and azetin-3-ol. The crude material was purified by flash chromatography (ethyl acetate/n-heptane) to yield the title compound as a white crystalline solid (yield 43%). MS (m/e): 367.9 (M+H$^+$, 100%).

b) [5-Methanesulfonyl-2-((S)-2,2,2-trifluoro-1-methyl-ethoxy)-phenyl]-[3-(4-trifluoromethyl-phenoxy)-azetidin-1-yl]-methanone

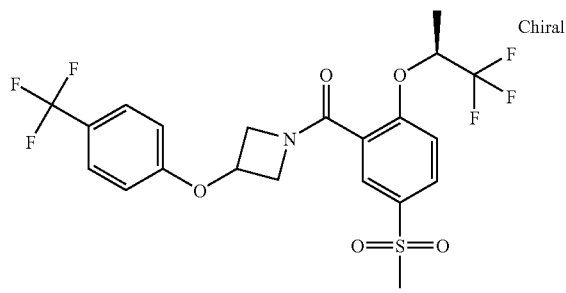

Prepared in analogy to Example 21(b) from (3-hydroxy-azetidin-1-yl)-[5-methanesulfonyl-2-((S)-2,2,2-trifluoro-1-methyl-ethoxy)-phenyl]-methanone and 4-fluorobenzotrifluoride. The crude material was purified by flash chromatography (methanol/dichloromethane) to yield the title compound as a white crystalline solid (yield 5%). MS (m/e): 512.5 (M+H$^+$, 100%).

Example 24

[5-Methanesulfonyl-2-((R)-2,2,2-trifluoro-1-methyl-ethoxy)-phenyl]-[3-(4-trifluoromethyl-phenoxy)-azetidin-1-yl]-methanone a) (3-Hydroxy-azetidin-1-yl)-[5-methanesulfonyl-2-((R)-2,2,2-trifluoro-1-methyl-ethoxy)-phenyl]-methanone

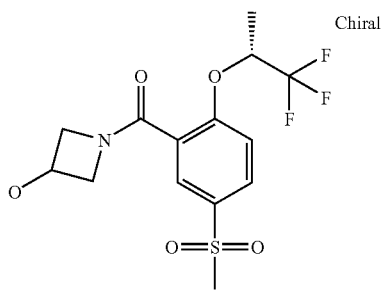

Prepared in analogy to Example 1 from 5-methanesulfonyl-2-((R)-2,2,2-trifluoro-1-methyl-ethoxy)-benzoic acid (Example A3(b)) and azetin-3-ol. The crude material was purified by flash chromatography (ethyl acetate/n-heptane) to yield the title compound as a white crystalline solid (yield 30%). MS (m/e): 368.0 (M+H$^+$, 100%).

b) [5-Methanesulfonyl-2-((R)-2,2,2-trifluoro-1-methyl-ethoxy)-phenyl]-[3-(4-trifluoromethyl-phenoxy)-azetidin-1-yl]-methanone

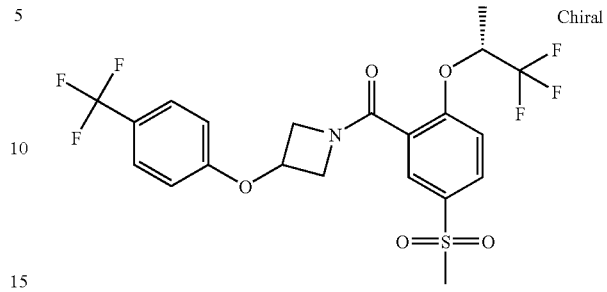

Prepared in analogy to Example 21(b) from (3-hydroxy-azetidin-1-yl)-[5-methanesulfonyl-2-((R)-2,2,2-trifluoro-1-methyl-ethoxy)-phenyl]-methanone and 4-fluorobenzotrifluoride. The crude material was purified by flash chromatography (methanol/dichloromethane) to yield the title compound as a white crystalline solid (yield 9%). MS (m/e): 512.3 (M+H$^+$, 100%).

Example 25

(5-Methanesulfonyl-2-morpholin-4-yl-phenyl)-[3-(4-trifluoromethyl-phenoxy)-pyrrolidin-1-yl]-methanone a) 3-(4-Trifluoromethyl-phenoxy)-pyrrolidine-1-carboxylic acid tert-butyl ester

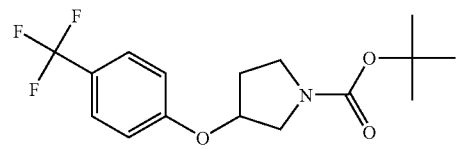

To a solution of 1.03 mmol 3-hydroxy-pyrrolidine-1-carboxylic acid tert-butyl ester in 15 ml tetrahydrofuran were added successively 1.23 mmol 4-hydroxybenzotrifluoride, 1.43 mmol triphenylphosphine and 1.43 mmol di-tert-butyl azodicarboxylate. The reaction mixture was stirred at 70° C. for 28 h and was then cooled to room temperature and concentrated in vacuo. The crude material was purified by chromatography (ethyl acetate/heptane) to afford the title compound as a white crystalline solid (yield 15%). MS (m/e): 276.1 ([M+H-Me$_2$C=CH$_2$]$^+$, 100%).

b) 3-(4-Trifluoromethyl-phenoxy)-pyrrolidine

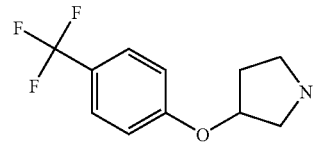

To a solution of 0.75 mmol 3-(4-trifluoromethyl-phenoxy)-pyrrolidine-1-carboxylic acid tert-butyl ester in 20 ml dioxane at 0° C. was added dropwise 9.20 mmol trifluoroacetic acid, and the reaction mixture was then stirred at RT for 3 h. The reaction mixture was then concentrated in vacuo, and the residue resuspended in ethyl acetate and washed with 1 M aqueous hydrochloric acid. The aqueous phase was separated and then made basic by addition of 1 M aqueous sodium hydroxide solution and subsequently extracted with ethyl acetate. The organic phase was dried over sodium sulfate and concentrated in vacuo to afford the title compound as a white amorphous solid (yield 69%). MS (m/e): 232.1 (M+H+, 100%).

c) (5-Methanesulfonyl-2-morpholin-4-yl-phenyl)-[3-(4-trifluoromethyl-phenoxy)-pyrrolidin-1-yl]-methanone

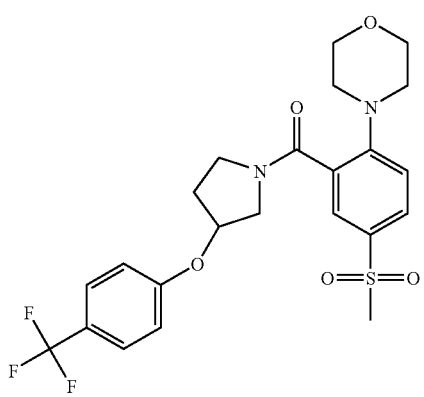

Prepared in analogy to Example 1 from 5-methanesulfonyl-2-morpholin-4-yl-benzoic acid (Example A4) and 3-(4-trifluoromethyl-phenoxy)-pyrrolidine. The crude material was purified by chromatography (methanol/dichloromethane) to yield the title compound as a white solid (yield 20%). MS (m/e): 499.4 (M+H+, 100%).

Example 26

4-Cyclopentyloxy-N-methyl-3-[3-(4-trifluoromethyl-phenoxy)-pyrrolidine-1-carbonyl]-benzenesulfonamide

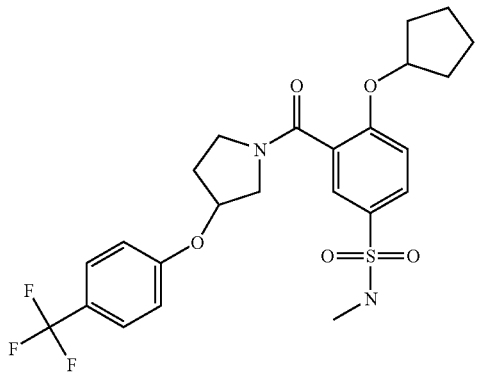

Prepared in analogy to Example 1 from 2-cyclopentyloxy-5-methylsulfamoyl-benzoic acid (Example A5) and 3-(4-trifluoromethyl-phenoxy)-pyrrolidine (Example 25(b)). The crude material was purified by chromatography (methanol/dichloromethane) to yield the title compound as an off-white solid (yield 11%). MS (m/e): 513.5 (M+H+, 100%).

Example 27

(2-Isopropylsulfanyl-5-methanesulfonyl-phenyl)-[3-(4-trifluoromethyl-phenoxy)-pyrrolidin-1-yl]-methanone

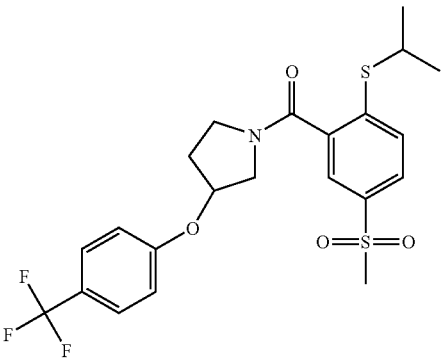

Prepared in analogy to Example 1 from 2-isopropylsulfanyl-5-methanesulfonyl-benzoic acid (Example A6) and 3-(4-trifluoromethyl-phenoxy)-pyrrolidine (Example 25(b)). The crude material was purified by chromatography (methanol/dichloromethane) to yield the title compound as a light brown solid (yield 42%). MS (m/e): 488.1 (M+H+, 100%).

The invention claimed is:
1. A compound of formula IB,

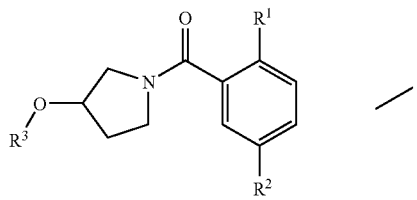

wherein
R$^1$ is —OR$^{1'}$, —SR$^{1'}$ or a heterocycloalkyl group selected from the group consisting of oxetanyl, tetrahydrofuranyl, tetrahydropyranyl, azetidinyl, pyrrolidinyl, piperidinyl, piperazinyl, morpholinyl, and thiomorpholinyl;
R$^{1'}$ is lower alkyl, lower alkyl substituted by halogen, or —(CH$_2$)$_n$-cycloalkyl;
R$^2$ is —S(O)$_2$-lower alkyl or —S(O)$_2$NH-lower alkyl;
R$^3$ is aryl or heteroaryl, each of which is unsubstituted or substituted by one to three substituents, selected from the group consisting of lower alkyl, lower alkoxy, CN, NO$_2$, —C(O)-lower alkyl, —C(O)O-lower alkyl, halogen and lower alkyl substituted by halogen; and
n is 1 or 2;
or a pharmaceutically acceptable acid addition salt thereof.
2. A compound of claim 1, wherein R$^2$ is —S(O)$_2$-lower alkyl.
3. A compound of claim 2, wherein R$^2$ is —S(O)$_2$-methyl.
4. A compound of claim 1, wherein R$^1$ is OR$^{1'}$ or SR$^{1'}$.
5. A compound of claim 4, wherein R$^1$ is OR$^{1'}$.
6. A compound of claim 5, wherein R$^{1'}$ is lower alkyl.
7. A compound of claim 5, wherein R$^{1'}$ is lower alkyl substituted by halogen.
8. A compound of claim 1, wherein R$^1$ is heterocycloalkyl selected from the group consisting of oxetanyl, tetrahydrofuranyl, tetrahydropyranyl, azetidinyl, pyrrolidinyl, piperidinyl, piperazinyl, morpholinyl, and thiomorpholinyl.
9. A compound of claim 1, wherein R$^3$ is heteroaryl which is unsubstituted or substituted by one to three substituents, selected from the group consisting of lower alkyl, lower alkoxy, CN, NO₂, —C(O)-lower alkyl, —C(O)O-lower alkyl, halogen and lower alkyl substituted by halogen.

10. A compound of claim 1, wherein $R^3$ is aryl is aryl which is unsubstituted or substituted by one to three substituents, selected from the group consisting of lower alkyl, lower alkoxy, CN, NO₂, —C(O)-lower alkyl, —C(O)-lower alkyl, halogen and lower alkyl substituted by halogen.

11. A compound of claim 10, wherein $R^3$ is phenyl which is unsubstituted or substituted by one to three substituents, selected from the group consisting of lower alkyl, lower alkoxy, CN, NO₂, —C(O)-lower alkyl, —C(O)O-lower alkyl, halogen and lower alkyl substituted by halogen.

12. A compound of claim 11, wherein the phenyl is unsubstituted.

13. A compound of claim 11, wherein the phenyl is substituted by one to three substituents selected from the group consisting of NO₂, —C(O)-lower alkyl, and lower alkyl substituted by halogen.

14. A compound of claim 13, wherein the phenyl group is substituted by lower alkyl substituted by halogen.

15. A compound of claim 14, wherein the phenyl group is substituted by trifluoromethyl.

16. A compound of claim 10, wherein $R^3$ is naphthyl which is unsubstituted or substituted by one to three substituents, selected from the group consisting of lower alkyl, lower alkoxy, CN, NO₂, —C(O)-lower alkyl, —C(O)O-lower alkyl, halogen and lower alkyl substituted by halogen.

17. A compound of claim 1, selected from the group consisting of

Rac-(2-isopropoxy-5-methanesulfonyl-phenyl)-[3-(4-trifluoromethyl-phenoxy)-pyrrolidin-1-yl]-methanone, Rac-(2-isopropoxy-5-methanesulfonyl-phenyl)-[3-(naphthalen-2-yloxy)-pyrrolidin-1-yl]-methanone, (5-methanesulfonyl-2-morpholin-4-yl-phenyl)-[3-(4-trifluoromethyl-phenoxy)-pyrrolidin-1-yl]-methanone and 4-cyclopentyloxy-N-methyl-3-[3-(4-trifluoromethyl-phenoxy)-pyrrolidine-1-carbonyl]-benzenesulfonamide.

18. A pharmaceutical composition comprising a therapeutically effective amount of a compound of formula IB

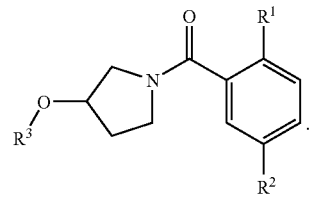

IB wherein $R^1$ is —OR¹', —SR¹' or a heterocycloalkyl group selected from the group consisting of oxetanyl, tetrahydrofuranyl, tetrahydropyranyl, azetidinyl, pyrrolidinyl, piperidinyl, piperazinyl, morpholinyl, and thiomorpholinyl;

R¹' is lower alkyl, lower alkyl substituted by halogen, or —(CH₂)ₙ-cycloalkyl;

$R^2$ is —S(O)₂-lower alkyl or —S(O)₂NH-lower alkyl;

$R^3$ is aryl or heteroaryl, each of which is unsubstituted or substituted by one to three substituents, selected from the group consisting of lower alkyl, lower alkoxy, CN, NO₂, —C(O)-lower alkyl, —C(O)O-lower alkyl, halogen and lower alkyl substituted by halogen; and n is 1 or 2;

or a pharmaceutically acceptable acid addition salt thereof and a pharmaceutically acceptable carrier.

* * * * *